United States Patent [19]
Pelosi, Jr.

[11] 3,962,284
[45] June 8, 1976

[54] 3-(5-ARYL-2-FURYL)-3-HYDROXYPROPIONIC ACIDS AND ETHYL ESTERS

[75] Inventor: Stanford S. Pelosi, Jr., Norwich, N.Y.

[73] Assignee: Morton-Norwich Products, Inc., Norwich, N.Y.

[22] Filed: Aug. 20, 1975

[21] Appl. No.: 606,244

[52] U.S. Cl............................ 260/347.5; 260/347.4; 260/347.8; 424/285
[51] Int. Cl.² ........................................ C07D 307/40
[58] Field of Search.................... 260/347.5, 347.4

[56] References Cited
UNITED STATES PATENTS
3,379,752  4/1968  Bolhofer .................. 260/473 A

OTHER PUBLICATIONS

Rathke, Chemical Reactions, vol. 22, pp. 423–431, 443, (1975).

*Primary Examiner*—Harry I. Moatz
*Attorney, Agent, or Firm*—Anthony J. Franze

[57] ABSTRACT

A series of 3-(5-aryl-2-furyl)-3-hydroxypropionic acids and ethyl esters are useful as antiinflammatory agents.

8 Claims, No Drawings

3-(5-ARYL-2-FURYL)-3-HYDROXYPROPIONIC ACIDS AND ETHYL ESTERS

This invention is concerned with chemical compounds. More particularly it is directed to a series of 3-(5-aryl-2-furyl)-3-hydroxypropionic acids and ethyl esters of the formula:

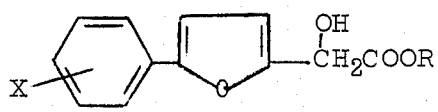

wherein X is 4-chloro, 3,4-dichloro, 4-bromo, 3-chloro, 4-fluoro or hydrogen and R is hydrogen or ethyl.

The members of this series of compounds possess pharmacologic activity. They are particularly useful as antiinflammatory agents as evidenced by their ability to inhibit edema induced in rats by the administration of carrageenin. Thus, when administered at a dose of 300 mg/kg suspended in a vehicle such as aqueous methyl cellulose per os to rats receiving carrageenin, edema associated with that substance is inhibited [Winter et al, P.S.E.B.M. 114:544 (1964)].

The compounds of this invention are currently preferably prepared according to the following scheme:

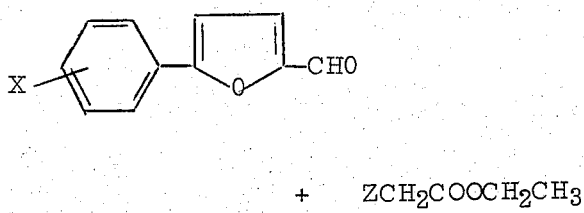

$$+ \quad ZCH_2COOCH_2CH_3$$

wherein X has the significance given above and Z is BrZn or Li followed by hydrolysis of the ester in the presence of base. The following examples illustrate the method of preparation.

EXAMPLE I

Ethyl 3-[5-(4-Chlorophenyl)-2-furyl]-3-hydroxypropionate

A solution of 48 g (0.23 mole) of 5-(p-chlorophenyl)-2-furaldehyde and 54 ml (0.48 mole) of ethyl bromoacetate in 340 ml of benzene was prepared by heating. A column (18 mm × 160 mm, jacketed) was filled to a height of 16 cm with granular zinc (20 mesh, activated by washing with 2% hydrochloric acid, water, 95% ethanol, acetone, anhydrous ether and drying in vacuo at ca. 100° for 0.5 hours) followed by 4 cm of glass helices. While circulating water at 80° through the jacket, the aldehyde solution was added from a heated addition funnel over a period of 4 hours. The solution which had collected was stirred for 15 minutes with 300 ml of cold 15% $H_2SO_4$. The organic layer was separated and washed successively with saturated $NaHCO_3$ solution and saturated NaCl solution. The benzene extract was dried ($Na_2SO_4$) and the solvent was removed on a rotary evaporator to give 80 g of residual oil. The crude oil crystallized after storage in a refrigerator for ca. 4 weeks. After trituration with hexane and filtration, the brown crystalline product was dissolved in 50 ml of toluene and 100 ml hexane was added. After seeding and cooling, the yield of product was 36 g. Two recrystallizations from toluene-hexane gave an analytical sample, m.p. 48°–49°.

Anal. Calcd. for $C_{15}H_{15}ClO_4$: C, 61.12; H, 5.13. Found: C, 61.45; H, 5.20.

EXAMPLE II

3-[5-(p-Chlorophenyl)-2-furyl]-3-hydroxypropionic Acid

A mixture of 3.0 g (0.01 mole) of the compound of Example I, 0.5 g (0.012 mole) of NaOH pellets, and 70 ml of 90% aqueous EtOH was heated under reflux for 1½ hours and was allowed to stand overnight. The mixture was made acidic with dilute HCl and was poured into 150 ml of an ice-$H_2O$ mixture. The solid was collected by filtration to give 1.6 g of crude product which was set aside. A second crop precipitated in the filtrate and was collected by filtration to give 0.7 g (26%) of product. Two recrystallizations from toluene gave an analytical sample, m.p. 107.5°–108.5°.

Anal. Calcd. for $C_{13}H_{11}ClO$: C, 58.55; H, 4.18. Found: C, 58.50; H, 4.13.

EXAMPLE III

3-[5-(3-Chlorophenyl)-2-furyl]-3-hydroxypropionic Acid Monohydrate

A mixture of 53 g (0.35 mole) of 5-(3-chlorophenyl)-2-furaldehyde, 50 g (0.30 mole) of ethyl bromoacetate, 350 ml of dry benzene and 175 ml of anhydrous ether was warmed to 30° with dissolution. A 50 ml portion of this solution and 5 crystals of iodine were added to a flamed-out flask containing 19 g. (0.30 mole) of Zn dust. The resulting mixture was heated to a gentle reflux and the remaining solution was added dropwise over a 1 hour period. After the addition was complete, the mixture was refluxed two additional hours, cooled and added to 250 ml of cold 10% sulfuric acid. After stirring for 30 minutes the benzene layer was separated, washed twice with cold 10% sulfuric acid, once with 10% sodium carbonate, once with water and dried over $MgSO_4$. The solvent was removed on the Calab evaporator yielding the crude ester.

A mixture of 37 g (0.125 mole) of the above ester, 163 ml of ethanol, 125 ml of 1 N NaOH solution and 250 ml of $H_2O$ was warmed at 45° for an hour and then cooled in an ice bath. A small amount of insoluble material was filtered and discarded. The filtrate was washed with ether and then made acidic with 10% hydrochloric acid. The resulting oil was extracted with ether and the combined ethereal extracts dried over $MgSO_4$. The solvent was removed on the Calab evaporator yielding a residual oil. This oil was taken to dissolution in toluene on the steam bath, cooled to room temperature and treated with hexane with a solid forming. The above procedure was repeated twice more and the resulting solid air-dried to yield 9 g (13% overall), m.p. 50°–52°.

Anal. Calcd. for $C_{13}H_{11}ClO_4 \cdot H_2O$: C, 54.84; H, 4.60. Found: C, 54.64; H, 4.37.

EXAMPLE IV

3-[5-(3,4-Dichlorophenyl)-2-furyl]-3-hydroxypropionic Acid

A. Lithium Bis(trimethylsilyl)amide

A flamed-out flask under a nitrogen atmosphere was charged with 125 ml of a hexane solution containing 0.25 mole of n-butyllithium. The flask was immersed in an ice bath and 42 g (0.26 mole) of hexamethyldisilazane was added dropwise over a 10 minute period. The ice bath was removed and stirring continued 10 additional minutes. The hexane was removed under reduced pressure with an oil pump to leave a white residual solid which was dissolved in 725 ml of tetrahydrofuran.

B. Lithio Ethyl Acetate

The reaction flask from above reaction was immersed in a dry-ice/acetone bath and stirred 15 minutes to insure temperature equilibration. After this time 22 g (0.25 mole) of ethyl acetate was added over a 10 minute period. Stirring at dry ice temperature was continued an additional 15 minutes to insure the complete formation of lithio ethyl acetate.

C. Ethyl 3-[5-(3,4-Dichlorophenyl-2-furyl]-3-hydroxypropionate

Using Gooch tubing 60 g (0.25 mole) of 5-(3,4-dichlorophenyl)-2-furaldehyde was added portion-wise to the solution of lithio ethyl acetate over a 10 minute period. The resulting mixture was stirred at dry ice-acetone temperature for an additional hour and then hydrolyzed by adding 75 ml of 20% hydrochloric acid all at once. The reaction was allowed to warm to room temperature. The organic layer was separated, the aqueous layer extracted with ether, and the combined organic solution dried over magnesium sulfate. The solvent was removed on the Calab evaporator yielding the crude ester as a residual oil.

D. 3-[5-(3,4-Dichlorophenyl)-2-furyl]-3-hydroxypropionic Acid

A mixture of 72 g (0.23 mole) of the above ester, 288 ml of ethanol, 230 ml of 1 N NaOH solution and 460 ml of water was warmed at 45° for 1 hour and then cooled to room temperature. A small amount of solid was filtered and discarded. The filtrate was extracted several times with ether and then made acidic with 20% hydrochloric acid. The resulting oil was extracted with ether and the combined ethereal extracts dried over $MgSO_4$. The solvent was removed in the Calab evaporator yielding a residual oil. This oil was taken to dissolution with toluene on the steam bath, treated with charcoal and filtered. The filtrate was cooled and the resulting solid filtered and air dried to yield 27 g (36% overall). An analytical sample was prepared by recrystallizing a sample a second time from toluene and drying in the vacuum pistol at room temperature, m.p. 95°–96°.

Anal. Calcd. for $C_{13}H_{10}Cl_2O_4$: C, 51.85; H, 3.35. Found: C, 51.78; H, 3.41.

EXAMPLE V

3-[5-(4-Bromophenyl)-2-furyl]-2-hydroxypropionic acid

A solution of 0.25 mole of lithio ethyl acetate (see Example IV) in 725 ml of tetrahydrofuran was treated portionwise with 63 g (0.25 mole) of 5-(4-bromophenyl)-2-furaldehyde while under a nitrogen atmosphere and at the temperature of dry ice - acetone. The resulting mixture was stirred in the cold for one additional hour and then 75 ml of 20% hydrochloric acid was added all at once. The reaction was allowed to warm to room temperature with near dissolution. The organic layer was separated, the aqueous layer was extracted with ether, and the combined organic solution was dried over $MgSO_4$. The solvent was removed on the Calab evaporator yielding the crude ester as a residual oil.

A mixture of 77 g (0.23 mole) of the above ester, 296 ml of ethanol, 227 ml of 1 N NaOH solution and 450 ml of $H_2O$ was warmed at 45° for 1 hour and then cooled in an ice bath. The resulting solid was filtered, washed with ether, stirred in 10% hydrochloric acid, and refiltered. This solid was warmed on a steam bath with 1000 ml of toluene and filtered hot. The insoluble material was set aside. The filtrate was cooled and the resulting solid filtered and air dried to yield 30 g (38% overall). An analytical sample was prepared by recrystallizing a sample from toluene and drying in the vacuum pistol at room temperature, m.p. 104°–107°.

Anal. Calcd. for $C_{13}H_{11}BrO_4$: C, 50.18; H, 3.56. Found: C, 50.31; H, 3.73.

EXAMPLE VI

3-[5-(4-Fluorophenyl)-2-furyl]-3-hydroxypropionic Acid

A solution of 0.25 mole of lithio ethyl acetate (see Example IV) in 725 ml of tetrahydrofuran was treated portionwise with 46 g (0.25 mole) of 5-(4-fluorophenyl)-2-furaldehyde while under a nitrogen atmosphere and at the temperature of dry ice-acetone. The resulting mixture was stirred in the cold for 1 additional hour and then 75 ml of 20% hydrochloric acid was added all at once. The reaction was allowed to warm to room temperature with dissolution. The organic layer was separated, dried over $MgSO_4$, and evaporated on the Calab evaporator yielding the crude ester as a residual oil.

A mixture of 58 g (0.21 mole) of the above ester, 220 ml of ethanol, 400 ml of $H_2O$ and 210 ml of 1N NaOH solution was stirred at room temperature for 2 hours. The reaction mixture was washed several times with ether, and the aqueous layer was then taken to a pH of 4 by the addition of 10% hydrochloric acid. The resulting solid was collected by filtration and recrystallized from toluene to yield 37 g (59% overall). An analytical sample was prepared by drying a sample in the vacuum pistol at room temperature, m.p. 120°–121°.

Anal. Calcd. for $C_{13}H_{11}FO_4$: C, 62.40; H, 4.43. Found: C, 62.45; H, 4.39.

EXAMPLE VII 3-(5-Phenyl-2-furyl)-2-hydroxypropionic Acid

A. Lithium N-Isopropylcyclohexylamide

A flamed-out flask under a nitrogen atmosphere was charged with 175 ml of a hexane solution containing 0.35 mole of n-butyllithium. The flask was immersed in an ice bath and 52 g (0.37 mole) of N-isopropylcyclohexylamine was added dropwise over a 10 minute period. The ice bath was removed and stirring was continued for 10 additional minutes. The hexane was removed under reduced pressure with an oil pump to leave a white residual solid which was dissolved in 1000 ml of tetrahydrofuran.

B. Lithio Ethyl Acetate

The reaction from above reaction was immersed in a dry ice-acetone bath and stirred 15 minutes to insure temperature equilibration. After this time 31 g (0.35 mole) of ethyl acetate was added over a 10 minute period. Stirring at dry ice temperature was continued an additional 15 minutes to insure the complete formation of lithio ethyl acetate.

C. 3-(5-Phenyl-2-furyl)-3-hydroxypropionic Acid

To a solution of 0.35 mole of lithio acetate in 100 ml of tetrahydrofuran was added dropwise over a 10 minute period a solution of 60 g (0.35 mole) of 5-phenyl-2-furaldehyde in 100 ml of tetrahydrofuran while under a nitrogen atmosphere and at the temperature of dry ice-acetone. The resulting mixture was stirred in the cold for 1 additional hour and then 75 ml of 20% hydrochloric acid was added all at once. The reaction was allowed to warm to room temperature and a small amount of solid was filtered and discarded. The organic layer was separated and dried over $MgSO_4$. The solvent was removed on the Calab evaporator yielding the crude ester as a residual oil.

A mixture of 121 g (0.35 mole) of the above ester, 340 ml of 1 N NaOH solution, 680 ml of water and 442 ml of ethanol was warmed at 45° for 1 hour and then cooled to room temperature. The resulting solution was washed with ether and then made acidic with 10% hydrochloric acid. The resulting solid was recrystallized from toluene and air dried to yield 25 g (32%). An analytical sample was prepared by recrystallizing a sample a second time from toluene and drying in the vacuum pistol at room temperature, m.p. 110°–111°.

Anal. Calcd. for $C_{13}H_{12}O_4$: C, 67.23; H, 5.21. Found: C, 67.27; H, 5.10.

What is claimed is:

1. A compound of the formula:

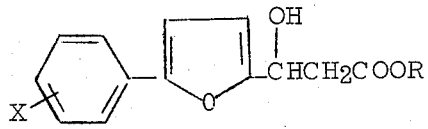

wherein X is 4-chloro, 3,4-dichloro, 4-bromo, 3-chloro, 4-fluoro or hydrogen and R is hydrogen or ethyl.

2. The compound ethyl 3-[5-(4-chlorophenyl)-2-furyl]-3-hydroxypropionate.

3. The compound 3-[5-(p-chlorophenyl)-2-furyl]-3-hydroxypropionic acid.

4. The compound 3-[5-(3-chlorophenyl)-2-furyl]-3-hydroxypropionic acid.

5. The compound 3-[5-(3,4-dichlorophenyl)-2-furyl]-3-hydroxypropionic acid.

6. The compound 3-[5-(4-bromophenyl)-3-hydroxypropionic acid.

7. The compound 3-[5-(4-fluorophenyl)-2-furyl]-3-hydroxypropionic acid.

8. The compound 3-(5-phenyl-2-furyl)-3-hydroxypropionic acid.

* * * * *

UNITED STATES PATENT OFFICE
CERTIFICATE OF CORRECTION

Patent No. 3,962,284      Dated     June 8, 1976

Inventor(s)    Stanford S. Pelosi, Jr.

It is certified that error appears in the above-identified patent and that said Letters Patent are hereby corrected as shown below:

Formula at column 1, line 10 should be:

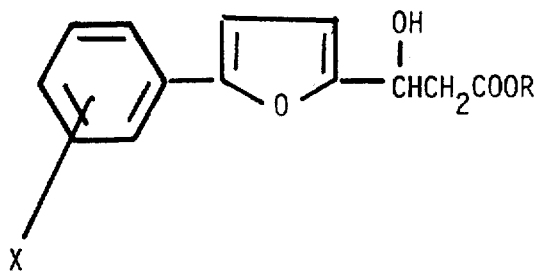

Column 3, line 64:    "2-hydroxypropionic" should be -- 3-hydroxypropionic --

Column 4, line 59:    "2-hydroxypropionic" should be -- 3-hydroxypropionic --

Column 5, line 14:    After "lithio" insert -- ethyl --

Signed and Sealed this

Fourteenth Day of September 1976

[SEAL]

Attest:

RUTH C. MASON            C. MARSHALL DANN
*Attesting Officer*         *Commissioner of Patents and Trademarks*